US00PP13271P3

(12) United States Plant Patent
Noodelijk

(10) Patent No.: US PP13,271 P3
(45) Date of Patent: Nov. 26, 2002

(54) CHRYSANTHEMUM PLANT NAMED 'AMPHION'

(75) Inventor: Robert Noodelijk, Woubrugge (NL)

(73) Assignee: Chrysanthemum Breeders Association NV (NL)

( * ) Notice: Subject to any disclaimer, the term of this patent is extended or adjusted under 35 U.S.C. 154(b) by 0 days.

(21) Appl. No.: 09/734,659

(22) Filed: Dec. 13, 2000

(65) Prior Publication Data

US 2002/0092079 P1 Jul. 11, 2002

(51) Int. Cl.[7] ..... A01H 5/00

(52) U.S. Cl. ..... Plt./298

(58) Field of Search ..... Plt./298, 286

*Primary Examiner*—Bruce R. Campell
*Assistant Examiner*—June Hwu
(74) *Attorney, Agent, or Firm*—Parkhurst & Wendel, L.L.P.

(57) ABSTRACT

A chrysanthemum plant named 'AMPHION' characterized by its small sized blooms with purple ray florets and prolific branching; natural season flower date August 26–31; blooming for a period of 5 weeks.

3 Drawing Sheets

BOTANICAL CLASSIFICATION

*Chrysanthemum morifolium* 'AMPHION'.

BACKGROUND OF THE INVENTION

'AMPHION' is a product of a breeding and selection program for outdoor pot mums (garden mums) which had the objective of creating new chrysanthemum cultivars with a daisy type flower, a natural season flower date around August 26–31; blooming for a period of 5 weeks. The new plant of the present invention comprises a new and distinct cultivar of Chrysanthemum plant. 'AMPHION' is a seedling resulting from the open pollination among groups of chrysanthemum cultivars maintained under the control of the inventor for breeding purposes. The new and distinct cultivar was discovered and selected as one flowering plant by Rob Noodelijk on a cultivated field in Rijsenhout, Holland in September 1998. The plant has been asexually reproduced by cuttings in greenhouses at Rijsenhout, Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
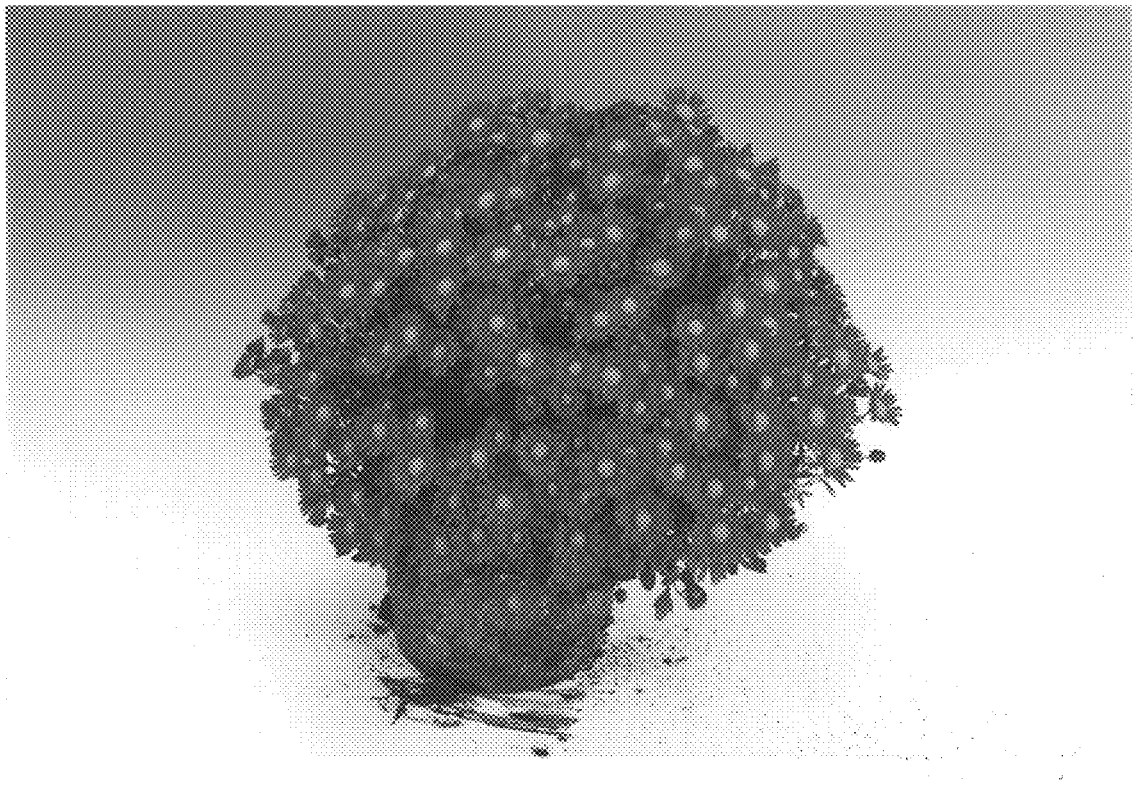
FIG. 1 shows a plant of the cultivar in full bloom.
Figure 2:
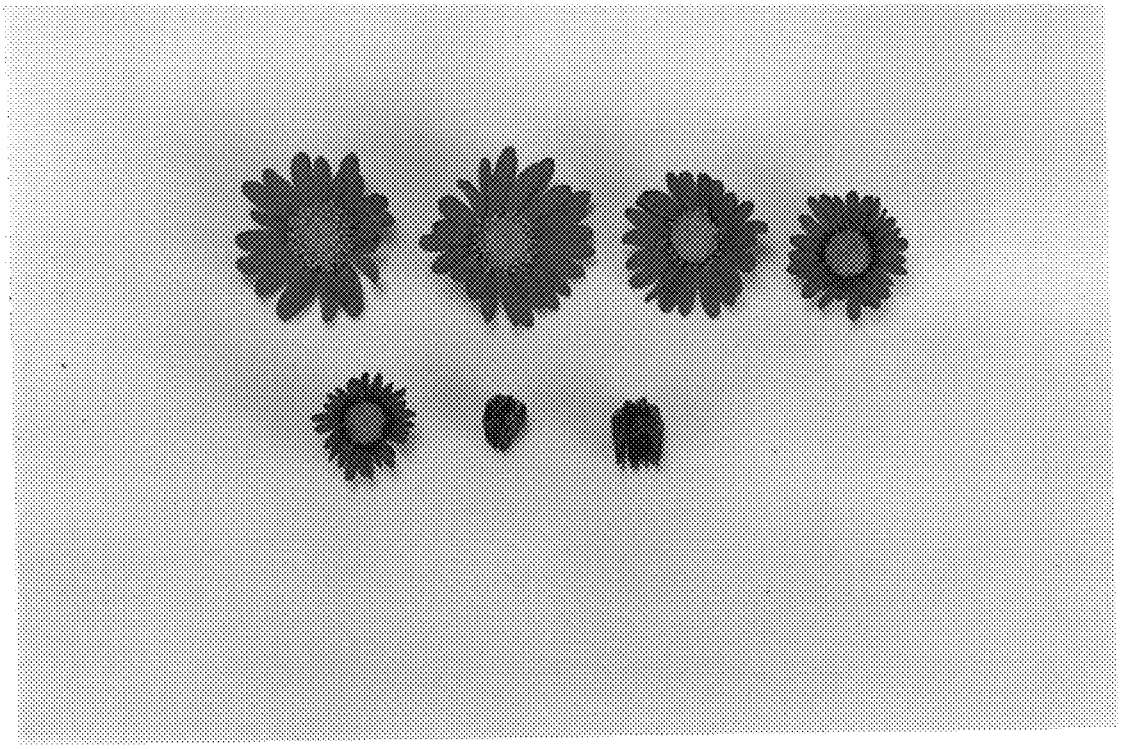
FIG. 2 shows the various stages of bloom of the new cultivar.
Figure 3:
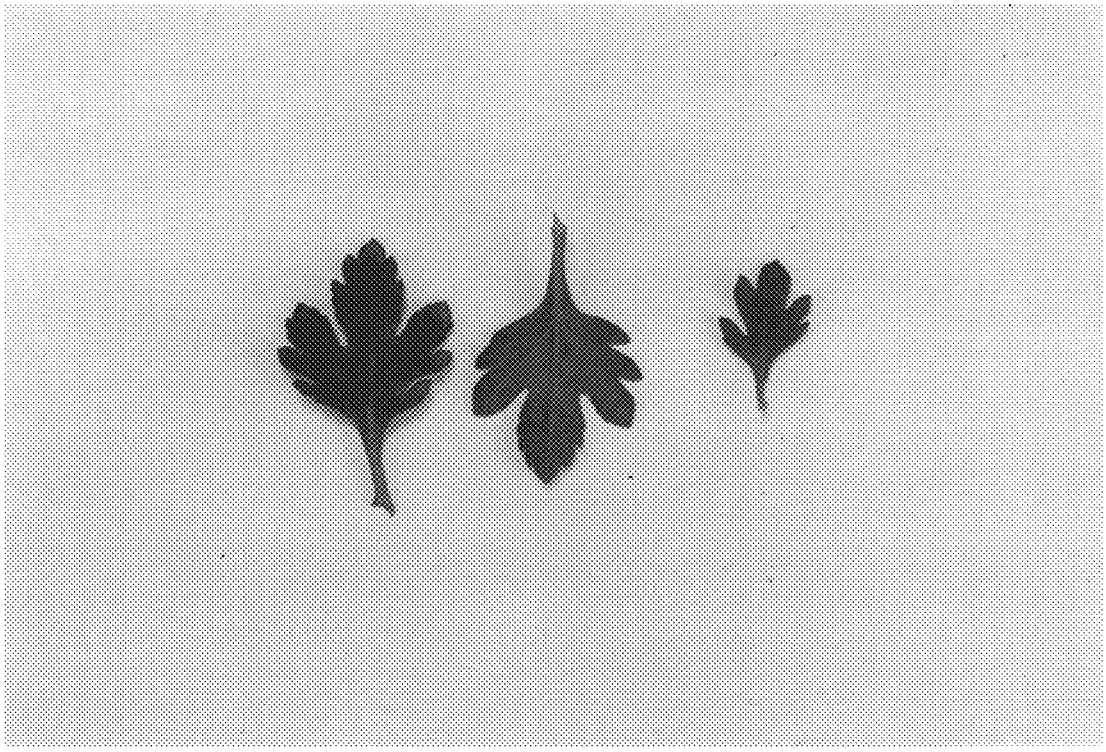
FIG. 3 shows the various stages of foliage and petiole of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 1999 and 2000. The natural blooming date of this crop was August 26–31 (week 35). The age of the observed plant was 13 weeks. The average height of the plants was 35–40 cms. No growth retardants were used. No tests were done on disease or insects resistance or susceptibility. No tests were done on cold or drought resistance. This new variety produces small sized blooms with purple ray florets and a yellow flower disc blooming for a period of 5 weeks.

From the cultivars known to inventor the most similar existing cultivar in comparison to 'AMPHION' is 'BOLD FELICIA'. When 'BOLD FELICIA' and 'AMPHION' are being compared the following differences are noticed: The differences of 'BOLD FELICIA' and 'AMPHION' are (1) Natural blooming date. 'AMPHION' flowers much earlier (2) Plant shape and branching. 'AMPHION' branches more prolific and has a more mounded plant.

The following is a description of the plant and characteristics that distinguish 'AMPHION' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1: Botanical Description of Cultivar Amphion

Bud:
- *Size.*—Small; cross-section 0.6 cm, height 0.6 cm.
- *Outside color.*—Red-purple 64 A.
- *Phyllaries.*—2 rows, length 7 mm, width 3 mm.
- *Involucral bracts among disc-florets.*—Not present.
- *Involucral bracts color.*—Green 147 B.

Bloom:
- *Type.*—Daisy.
- *Height.*—Flat, 1.0–1.3 cm.
- *Size.*—Small.
- *Fully expanded.*—2.5–3.0 cm.
- *Number of blooms per branch.*—Approx. 6–7 blooms per branch.

*Performance on the plant.*—5 weeks.
*Seeds* (*if crossed*).—Produced in large quantities, oval shaped. Grey-brown 199 A, 1.5 mm in length.
*Fragrance.*—Typical chrysanthemum, slight.

Color:
*Center of the flower* (*disc-florets*).—Immature yellow-green 150 B. Mature yellow 154 B.
*Color of upper surface of the ray-florets.*—Red-purple 72 A.
*Color of the lower surface of the ray-florets.*—Red-purple 72 D.
*Tonality from distance.*—A garden mum with purple flowers and a yellow disc.
*Color of the upper surface of the flowers after aging of the plant.*—Red-purple 72 C.

Ray florets:
*Texture.*—Upper and under side smooth.
*Number.*—23–25.
*Cross-section.*—Concave, two keels.
*Longitudinal axis of majority.*—Straight.
*Length of corolla tube.*—Very short, 0.2–0.3 cm.
*Ray-floret margin.*—Entire.
*Ray-floret length.*—0.7–1.0 cm.
*Ray-floret width.*—0.3–0.4 cm.
*Ratio length/width.*—Medium.
*Shape of tip.*—Pointed.

Disc florets:
*Disc diameter.*—1.0–1.2 cm.
*Distribution of disc florets.*—Numerous, clearly visible at all stages of flowering.
*Shape.*—Tubular.
*Color.*—Yellow-green 150 B.
*Receptacle shape.*—Conical raised.

Reproductive organs:
*Stamen* (*present in disc florets only*).—Thick, 3 mm in length.
*Stamen color.*—Yellow-green 144 A.
*Pollen.*—Present.
*Pollen color.*—Yellow 9 A.
*Styles.*—Thin.
*Style color.*—Yellow-green 144 A.
*Style length.*—4 mm.
*Stigmas.*—Yellow-green 144 A.
*Stigma width.*—1 mm.
*Ovaries.*—Enclosed in calyx.

Plant:
*Shape.*—Grown as a spray-type pot-mum, outdoor mounded and round.
*Growth habit.*—Spreading.
*Growth rate.*—Rapid.
*Height.*—35–40 cm.
*Width.*—40–45 cm.
*Stem color.*—Green 147 B.
*Stem strength.*—Weak.
*Stem brittleness.*—Absent.
*Stem anthocyanin coloration.*—Present, a thin layer of greyed-red 181 A mainly at the base of the stem.
*Length of lateral branch.*—From top to bottom 11–12 cm.
*Lateral branch color.*—Green 147 B.
*Lateral branch, attachment.*—Strong.
*Branching* (*average number of lateral branches*).—Mounding and prolific with 7 breaks after pinching.
*Peduncle length.*—2.5–3.0 cm.
*Peduncle color.*—Green 147 B.
*Natural season blooming date.*—August 26–31.

Foliage:
*Color of mature leaves.*—Upper side green 147 A. Under side green 147 B.
*Color of immature leaves.*—Upper side yellow-green 146 A. Under side yellow-green 146 B.
*Size.*—Very small; length 3.5 cm, width 3.0 cm.
*Quantity* (*number per lateral branch*).—6–7.
*Shape.*—Pinnatifid.
*Texture upper side.*—Glabrous.
*Texture under side.*—Pubescent.
*Venation arrangement.*—Palmate.
*Shape of the margin.*—Serrated.
*Shape of base of sinus between lateral lobes.*—Acute.
*Margin of sinus between lateral lobes.*—Diverging.
*Shape of base.*—Asymmetric.
*Apex.*—Cuspidate.

TABLE 2

Differences wtih the comparison varieties (when grown under the same conditions)

| | 'AMPHION' | 'BOLD FELICIA' |
|---|---|---|
| Natural blooming Date | August 26–31 | September 18–22 |
| Plant shape and branching | Mounded plant and very prolific branching | Somewhat more upright Plant and rich branching |

I claim:

1. A new and distinct variety of chrysanthemum plant as described and illustrated.

* * * * *